United States Patent [19]

Bilciurescu

[11] Patent Number: 4,592,729
[45] Date of Patent: Jun. 3, 1986

[54] STRIP-HOLDER FOR INTERDENTAL THERAPY

[76] Inventor: Andrei S. Bilciurescu, Kaiserplatz 14, 53 Bonn-1, Fed. Rep. of Germany

[21] Appl. No.: 717,753

[22] Filed: Mar. 29, 1985

[30] Foreign Application Priority Data

Apr. 14, 1984 [DE] Fed. Rep. of Germany ....... 3414192

[51] Int. Cl.⁴ ............................................... A61C 3/06
[52] U.S. Cl. ...................................... 433/142; 132/91
[58] Field of Search ............... 433/142, 147, 146, 125; 132/91, 92 R, 92 A

[56] References Cited

U.S. PATENT DOCUMENTS

| | | | |
|---|---|---|---|
| 1,050,469 | 1/1913 | Keifer | 433/142 |
| 1,201,875 | 10/1916 | Russ | 433/142 |
| 1,415,765 | 5/1922 | Bailey | 132/91 |
| 2,217,917 | 10/1940 | Munro | 132/92 R |

FOREIGN PATENT DOCUMENTS

| | | | |
|---|---|---|---|
| 377764 | 6/1923 | Fed. Rep. of Germany | 433/142 |
| 1101552 | 10/1955 | France | 433/142 |

Primary Examiner—John J. Wilson
Attorney, Agent, or Firm—Pollock, Vande Sande & Priddy

[57] ABSTRACT

The present invention refers to a strip-holder which is used in interdental therapy. The main object of the invention is to produce a strip-holder in which the abrasive steel-strip or the steel-sawblade, which is used for the reduction of the tooth width or for the abrading, cleaning and the prophylactic treatment of tooth and filling surfaces in the interdental space, can be easily and quickly inserted into the bow frame of the strip-holder and then tensed. The inventive strip-holder comprises a handle, a flat steel-bow or steel-frame and a gripping device, made of drawn-rod material, for the fixing and tensing of the steel-strip, which is inserted over the outer opening of the steel-bow into grip-slots. These slots are at the two opposite ends of the steel-bow and are cut at these ends into the rod material in such a way as to be slightly wider than the thickness of the steel-strips. The bow-half adjoining the handle of the strip-holder is part of the quick-tensing and gripping-device for the tape-like steel-strip or steel-sawblade.

12 Claims, 4 Drawing Figures

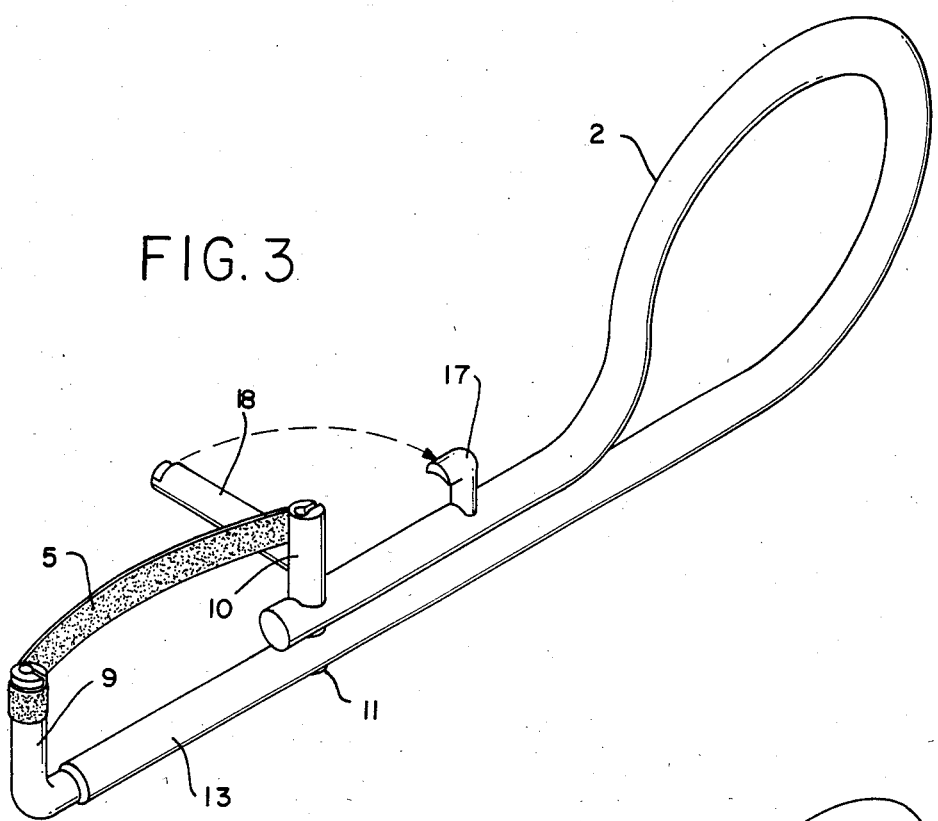
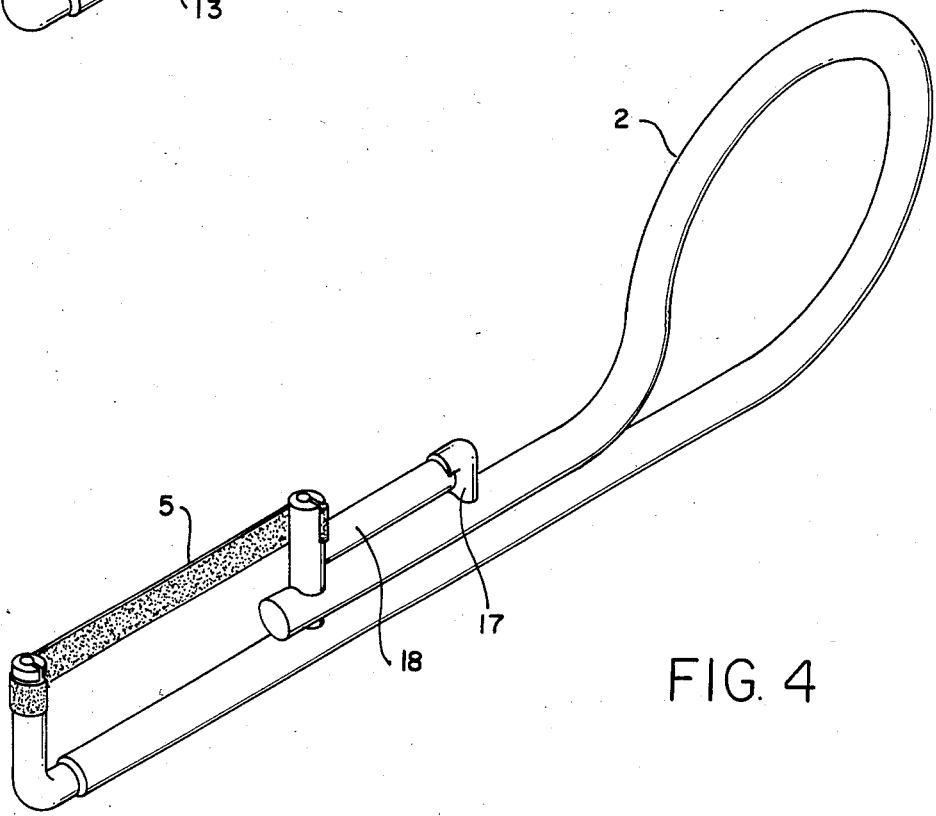

STRIP-HOLDER FOR INTERDENTAL THERAPY

TECHNICAL FIELD

The invention at issue deals with a strip - holder for interdental therapy, e.g., for the reduction of the tooth width or for the abrading, cleaning, and the prophylactic treatment of tooth and filling surfaces in interdental space. The stripes used in the holder are abrasive steel-bands or tensed steel sawblades, necessary for the prophylactic treatment.

BACKGROUND ART

The familiar model of known strip-holders consists of a handle, a steel - bow, and a gripping device for the fixing and tensing of a steel - strip covered on one side or both with abrasive material. The steel-strip is inserted over the outer opening of the steel - bow into the grip - openings, i.e., the gripping - clutches cut into the opposite ends of the steel - bow, and then tensed with a six - edge spanner. After fixing the steel-strip in the gripping - clutches, it is tensed with a six - edge spanner engaging the gripping - clutches and by means of a tensing - roller holding the forks of the steel - bow.

Although such an appliance, manufactured by the LM firm in Turku, Finland—by contrast with other such appliances in use with a cutting - disc fitted on to a handgrip, makes possible accurate approximal abrasion, particularly of the bigger teeth with a narrow cervix and a wider incisive tooth - edge, whereby the extent of the approximal reduction of the tooth width—through the use of one- or two - sided strips with increasing abrasive granulation, can be controlled, and also the risk of soft tissue injury is substantially reduced, in practice however, this familiar strip - holder has still disadvantages.

Thus the device is containing a lot of moving parts the maintenance of which requires the use of graphite grease or machine oil, so that the sterility of the appliance cannot be absolutely ensured. Further, it is extremely cumbersome to insert the steel - band between the gripping - clutches since it can only be replaced after disengaging the tensing - roller and opening the gripping - clutches with a six - edge spanner while pressing with the finger against the tensed steel-band. The fixing and tensing of a new steel - band consequently requires, in reverse order, its insertion into the gripping - clutches, i.e., grip - openings, its fixation in the grip - openings of the gripping - clutches and, with the help of a six - edge spanner, in the gripping mechanism. Subsequently, the excess steel - band must be removed with special pliers and the fork of the strip - holder must be properly set, i.e., tensed, by engaging and adjusting the tensing-roller.

Since, for the use of the strip - holder in interproximal space, the steel - band must be moved to and fro, and since its bow consists of two forks running parallel to each other above the gripping - clutches, the fork ends and the gripping - clutches must be introduced deeply into the mouth during therapy.

DISCLOSURE OF THE INVENTION

The main aim of this invention is to construct a new strip - holder for interdental therapy of the type mentioned in the beginning using steel-strips, whereby these abrasive steel - bands, or tensed steel sawblades can be easily and quickly inserted into the bow frame of the strip - holder, and then tensed.

This aim is achieved by suggesting a strip - holder for interdental therapy of the type mentioned before consisting out of a flat and somewhat U-shaped-bow made of drawn - rod material and which has an outer opening forming two bow - ends into which grip-openings, i.e., grip - slots, are cut in such a way as to be slightly wider than the thickness of the steel - strip; and the bow - half adjoining the handle of the steel - bow is part of a quick - tensing and gripping - device for the tapelike steel - strip.

Thus, pursuant to this invention, the steel - strip is set within the flat U-shaped steel - bow designed expressly for the purpose of tensing the steel-strip, whereby the handle is attached onto one bow - half, outside the bow itself. This part of the bow - half is simultaneously an element of the quick - tensing/grippingdevice for the tape - like steel - strip to be inserted into the grip - openings, i.e., grip - slots, at the bow - ends, after its ends have been folded. The length of the ends of the steel - strip to be inserted in the grip - slots is defined automatically by the depth of the slots being substantially the rod - diameter. The grip - slots are only slightly wider than the thickness of the steel - strip, so that the ends of such a strip of a given length can be inserted into the grip - slots and then - by means of the handle tensing the range of the rod - shaped fork - ends can be fixed and tensed between the grip - slots in the two opposite rod - shaped fork - ends.

Consequently, in the newly invented strip - holder, the length of the steel - strip, the distance between the external ends of the U-shaped steel-bow, the positioning and direction of the grip-slots and the tension range of the steel - strip (from the grip - slots to the remaining circumference of the bow - ends) are to be determined in such a way that—e.g., by turning the quick - tensing/gripping - device in the handle, the steel - strip, found between the ends of the U-shaped steel-bow, should diminish lengthwise by the desired extent, which is necessary to produce the necessary tension in the steel - strip and that to the contact - surface of the rod - shaped fork - ends. The latter producing the force holding the steel - strip in the slots between the fork - ends.

The quick - tensing/gripping - device is functionally reliable and easy to manufacture; in the handle - adjoining bow - half, the internal part of the bow - end with its grip - slot becomes a turning/locking - peg lying perpendicular to the prolongation of the frame. The turning - peg is operated by means of a T-shaped pivoting lever projecting from it which can be fixed into a catch on the handle of the strip - holder.

It is important for this quick - tensing/gripping - mechanism, based on the turning of the peg, i.e. the internal steel - bow - end, that the size of the outer opening of the U-shaped bow, i.e., the distance between the two bow - ends should hardly change during the tensing of the steel-strip and the employment of the strip - holder. For this reason, the steel - bow and preferably the entire strip - holder, including its handle, is to be made of a suitably thick V2A - steel-flat drawn - rod material. The frame - piece of the U-shaped steel - bow is continued, preferably through the prolongation of the drawn - rod, with a prolongation - piece, into the actual handle of the strip - holder, after which the rod, in the shape of a loop, is brought back towards and attached to the beginning of the frame of the U-shaped steel - bow, where it will serve as a reinforcement - segment running parallel to the prolongation - piece, to which it will be fastened in at least two places.

The attachment is effected at the beginning of the handle by a fixed catch - pin, introduced through boreholes made into both rods, which serves simultaneously as a catch for the lever of the turning/locking - peg of the U-shaped steel-bow.

Towards the interior bow - half, the two parallel rods will be fastened through the turning/locking - peg itself which pierces, through holes, both rods in the shape of a tapered shaft - segment and is fixed, through mobile riveting on the surface of the external rod forming the frame - prolongation.

The lever for the turning and locking of the peg - shaped interior bow - end is attached to the latter as a T-shaped projection in the form of a longish rod - piece, so that the relatively considerable force (due to the leverage effect, i.e., occurring torque) necessary for the tension of the steel - strip can be easily summoned. In order to secure the lever, in the tense state of the steel - strip, a catch standing out against the lever is set on the catch - pin, under the reinforcement segment, under which the lever-end can lock.

Consequently, the size of the steel - strip and the distance between the outer bow - ends and each grip - slot is to be determined in such a way that the lever, in the tense state of the strip - holder, comes to lie under the reinforcement - segment, i.e., the prolongation - piece, and, thus, before or under the catch - pin and its catch - piece.

By placing the reinforcement - segment in the region of the turning/locking - peg and of the catch-pin, and also because of the hardly flexible material structure of the fork - ends, preferably of V2A - steel - the necessary accuracy of the fork opening size is insured also in the tense state of the strip - holder; and the position of the lever under the catch - piece is ensured through almost complete inward immovability (i.e., towards the fork - opening) of the turning/locking - peg, in the tense state of the strip. The lever comes to be in this position after it has been swung together with the turning/locking - peg from its position, at first parallel to the frame of the U-shaped steel - bow, to an inclined position under the catch - piece.

The size of the grip - slot width in the fork-ends where the ends of the abrasive band or the sawblades are fixed simply by their insertion, followed by their folding around the external perimetral surface of the fork - ends, is dependent upon the strength of the abrasive band or the sawblade. It has been shown that it is possible to fix a strip or a blade 0.05–0.02 mm. thick in a slot merely 0.25 mm. wide, with an inner fork opening size of 2.8 cm. (in the lax state of the strip - holder), an inner spacing of the grip - slots of about 3.2 cm, and a 0.4–0.5 cm. diameter of the round profile rod, with sufficient reliability. In a preferred embodiment the rod of the fork - ends exhibits an inner central bore of about 1.5 mm diameter. Thus it is much easier to cut the grip - slots in the V2A - steel material to the inner bore than to cut the slots in a solid rod material.

The invention will be further explained with the help of a prototype and with references to its drawings.

BRIEF DESCRIPTION OF THE DRAWINGS

In The drawings:

FIG. 1 is a lengthwise view of the flat - shaped strip - holder which, including its handle, is substantially made of drawn - rod material; and FIGS. 2, 3 and 4 are schematic illustrations of the tensing procedure of the inserted steel-strip (whose ends are in the grip-slots

BEST MODE FOR CARRYING OUT THE INVENTION

Figures 1, 2:
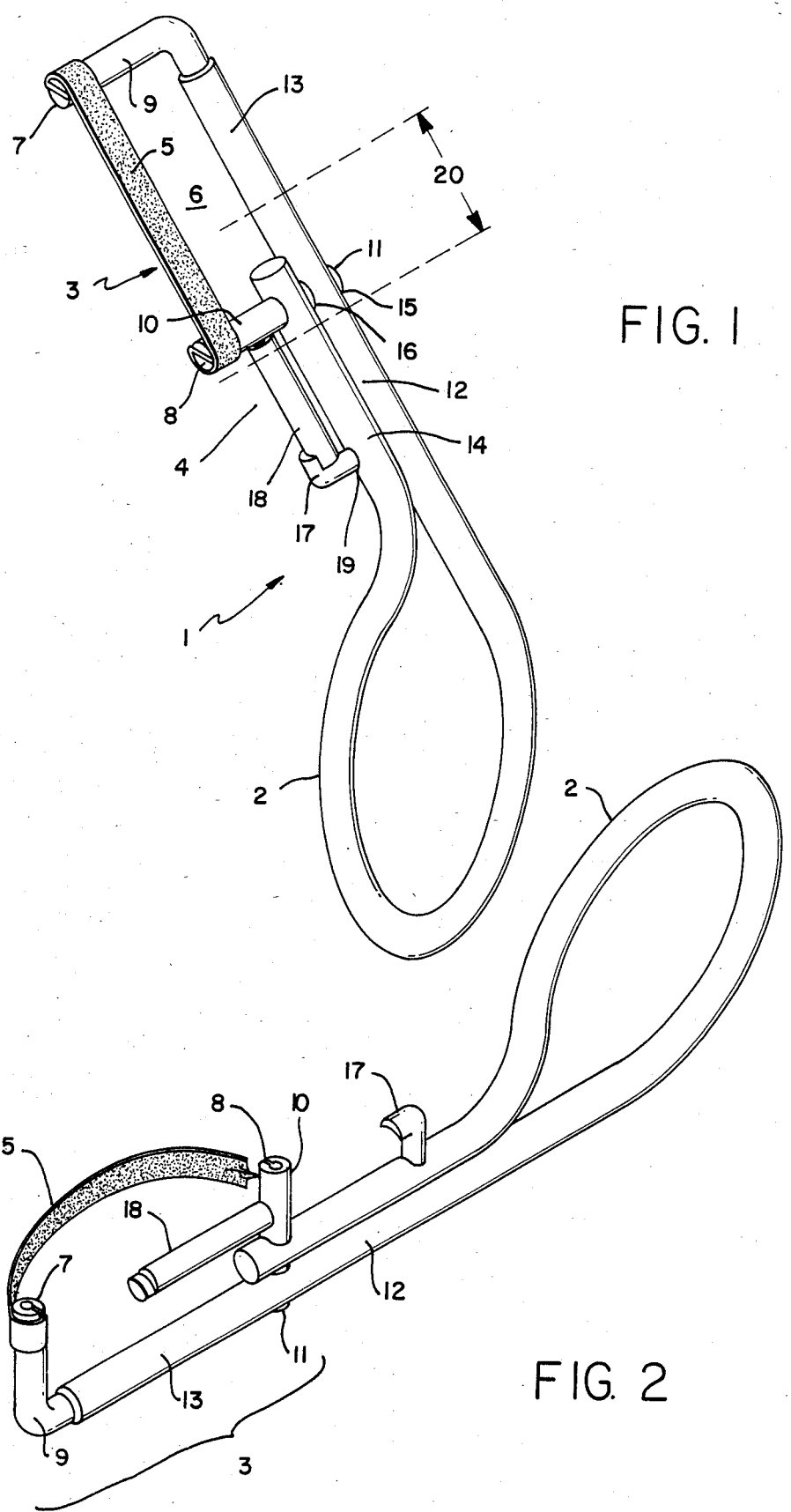

The strip - holder 1 in FIG. 1, the V2A - steel-strip 5 of which has a layer of abrasive material for the abrasion of tooth and filling surfaces as well as other purposes, is shown enlarged. The length of the strip - holder 1, as shown in the drawings, is about 12 cm., its handle 2 having a length of about 5 cm. from the catch - pin 19 downwards.

The remaining part of the strip - holder consists of a flat U-shaped steel - bow 3—which, like the rest of the strip - holder, is made of a 4 cm. long V2A - steel drawn - rod—and a prolongation - piece 12, i.e., reinforcement - segment 14, 2 cm. long, placed between the handle 2 and the U-shaped steel - bow 3.

The U-shaped steel - bow 3 consists of a frame-piece 13, attached straight to the prolongation-piece 12, of an external curved - piece ending with the bow - end 9, and of a turning - peg 11 - running both rods 12, 14 and being perpendicular to the frame 13, i.e., to the prolongation - piece 12, which, in its lax state, i.e., without a strip, runs parallel to the external curved - piece forming the box - end 9 of the fork or of the steel - bow 3.

Thus, an opening 6 facing away from the frame-piece is formed between the bow - ends 9, 10, which has a height of 1.2 cm. from the frame piece 13 to the bow - ends 9, 10. This height is sufficient for the performance of interdental therapy, especially for the lateral teeth, whereby the steel - strip to be inserted into the steel - bow 3 is 3–4 mm. wide.

The steel - strip 5, with its ends inserted into the small grip - slots 7, 8 can be tautly tensed quickly and safely through a quick - tensing/gripping - device 4 in the bow - half 20 adjoining the handle 2, so that precision work in the mouth is rendered possible, whether it is accurate approximal enamel abrasion or the separation of abstructed teeth, in which case a sawblade is used.

By contrast with the aforementioned LM - band - holder with gripping - clutches and a fork - shaped curved handpiece, it is only the anterior part of the strip-holder, i.e., the frontal part of the steel-bow 3 with its external bow - piece 9, that gets inserted into the patient's mouth. Consequently, the patient does not need to open his mouth so wide during lower - maxillary therapy. Besides, the risk of soft tissue injury is lower by manipulation of the strip-holder.

Pursuant to this invention, the tension of the steel-strip 5 is effected right in the region of the handle 2 - adjoining bow - half 20 ; safe and taut tensing of the steel - strip 5 between the ends 9, 10 of the steel - bow 3 is rendered possible by the quick - tensing/gripping - device 4. The tension is effected by the simple insertion of the ends of the steel - strip 5 into the grip - slots 7, 8 of the bow - ends 9, 10 and an appropriate turn about a 180° angle of the turning/locking - peg 11 forming the interior end - piece of the steel - bow 3. The peg 11 is tapered at its upper - end and fixed in the boreholes 15, 16 of the two parallel running rod - pieces, of the prolongation - piece 12 and the reinforcement - segment 14. The swing of the turning - peg 11 is effected by a T-shaped lever 18 attached to the peg 11, approximately in its middle, and pointed towards the handle.

are in the grip-slots of the U-bow by swinging the turning/locking-peg, i.e., the internal bow-end, with the T-shaped lever projecting from it.

The locking of the steel - strip 5, in its tense state, is effected by swinging the lever 18 under a protruding catch 17 of the catch - pin 19, which is placed towards the handle 2 at about a distance from the turning-peg 11 equal to the length of the lever 18.

The mounting, i.e., attachment, of the lever 18 onto the turning - peg 11 is so effected that the former, which, in the tense state of the steel - strip 5, can be swung right under the catch - pin, locks in the protrusion of the catch - piece 17, whereby the turning - peg 11 bends.

The width of the U-shaped bow - opening diminishes in this tense state from 2.8 cm. to 2.75 cm., while the entire length of the steel - strip 5, which is inserted into the slots 7, 8 and folded round the ends of the steel - bow 3, is 5.0 cm.

While one deliberately makes allowance for a slight bending of the turning - peg 11, in order for the lever 18 to be locked under the catch - piece 17, in the tense state of the steel - strip, it is particularly important to manufacture the U-shaped steel - bow 3 and the turning/locking - peg 11 with as much accuracy and shape stability as possible. This is partially effected through accurate determination of the diameter of the round-profile rod; the endpieces of the steel-bow 3 have a diameter of 0.4 cm. and the upper frame - piece 13, the prolongation - piece 12, and handle 2, and the reinforcement - segment 14 have a diameter of 0.5 cm. The turning - peg 11 is placed through the prolongation - piece 12 and also through the reinforcement - piece 14 which runs below the former over a length of 3.5 cm., so that the strip-holder has an area of greater stability around the turning - peg 11.

The lever 18, which in the tense state of the steel-strip gets locked under the catch - piece 17, functions as additional reinforcement.

The insertion of the 5.0 cm. long steel - strip alongside the outer opening 6 of the steel - bow 3, over the external perimetral surface of the bow - end piece, is presented schematically, in a chronological order, in FIG. 2, FIG. 3 and FIG. 4.

FIG. 2 is a frontal view of the bow - ends 9, 10 with their 0.25 mm. wide grip - slots 7, 8, which are at the beginning of the tensing procedure all directed perpendicular to the plane of the steel-strip and opposite to each other. By turning the peg 11, i.e., by swinging the lever 18 projecting laterally from it, the steel - strip 5 is folded partially round the circumference of the bow - ends 9, 10. By turning the peg 11, i.e., the grip - slot 8, by 180°, the steel - strip 5 is tensed between the two bow - ends 9, 10 as in FIG. 4, while it has its ends secured in the slots 7, 8. This firm and taut position is effected, on the one hand, by folding the steel-strips ends and then inserting them into the grip-slots 7, 8 which are only slightly wider than the thickness of the steel - strip (0.25 mm. wide for the 0.05 -0.2 mm. thick band), on the other hand, this remarkably high stability of the steel - strip folded around the round - profile rod results from the considerable length of 2.0 cm. over which the steel-strip 5 is tautly in direct contact with the rod surface of the bow - ends 9,10. (rod diameter 4 mm).

In this respect, an accurate correlation is required between the length of the steel - strip 5, the outer distance between the external surfaces of the bow-ends 9, 10 of the U-shaped steel - bow 3, and the extent of the strip tension - range, i.e., 2.0 cm., from the grip - slots 7, 8 to the remaining circumference of the bow - ends.

This relation can be adjusted so that the lever 18, projecting from the peg 11 in a T-shaped angle, swings simultaneously under the area of the prolongation - piece 12, i.e., of the reinforcement-segment 14, and locks under the catch - piece 17, being in the plane of the flat - shaped strip - holder.

Thus, this strip - holder for sawblades and steel-bands covered on one side or both with abrasive material is, on the one hand, in its direct handling for interdental therapy, lighter and safer to operate than the state - of - the - art familiar LM - band-holder, on the other hand, as regards its actual technical maneuverability, it is also markedly simpler, quicker, and more convenient to handle; the steel-strips can be removed quite lightly and quickly from the strip - holder and replaced by new ones. As the tension in the steel-strip 5 is very high these may be used also in the form of saw-blades for separating two near-by teeth.

Other possibilities are the approximal reduction of the tooth - width in the region of the incisive and premolar teeth, as orthodontical therapy; the contouring of outstanding fillings before the application of band - appliances; the separation of close-standing or anatomically wrongshaped teeth before the application of an orthodontical band - appliance; the check for the possible occurrence of tooth - gluing after the employment of the "adhesive - bracket-technique"; the alignment of teeth, the removal of interdental tartar and the smoothing and polishing of plastic, silicate, and amalgam fillings.

The best mode of carrying out the invention is principally explained in the description of the drawings (FIG. 1–FIG. 4 ).

As clearly shown, the grip-slots 7,8 at the bow-ends 9,10 extend through the center of the rod-material for substantially about the diameter of the rod.

Instead of a central bore in the middle of the bow-ends, there is used to cut the grip-slots in the steel material only a small bore eccentric to the rod-axis. Thus, the rod-material is weakened only to a small extent, and, nevertheless, cutting of the grip-slots to the desired length of the folded ends of the steel-strips is simplified.

According to FIG. 2, to facilitate introduction of the steelstrip 5, the grip-slots 7,8 should be directed perpendicular to the plane of the tensed strip between the bow-ends. The grip-slot 7 in the bow-end which is attached as one-piece to the frame-piece 13 at the outer end of the strip-holder should open to the opposite side of the opening of the grip-slot 8 which is located at the turnable peg. 11. Thus, by a 180 degree turn of the peg 11, the steel-strip 5 is folded around the half circumference of the bow-end 9 and also corresponding around that half circumference of the bow-end 10. According to FIG. 4, the tension-ranges around the rods of the bow-ends 9,10, have the same length and the grip-slots are directed and open to the same direction.

INDUSTRIAL APPLICABILITY

It is evident according to the above-mentioned that the inventive "strip-holder" has a far range of industrial applicability.

I claim:

1. A strip-holder for interdental therapy comprising a handle, a steel-bow, a tape-like steel-strip, and a quick-tensing and gripping-device providing grip-openings at opposite ends of said steel-bow for fixing and tensing the tape-like steel-strip over an outwardly facing opening of the steel-bow, wherein:

said steel-bow is substantially flat, approximately U-shaped, and made of drawn-rod material;

said grip-openings are cut in said steel-bow ends so as to provide grip-slots having only a slightly greater width than the thickness of the tape-like steel- strip;

said handle is attached to a portion of said steel-bow and extends outside the bow itself, this bow portion adjoining the handle being part of the quick-tensing and gripping-device for the tape-like steel strip and comprising an internal bow-end having a turning and locking-peg which is pivotally attached to a frame-piece of the U-shaped steel-bow and is perpendicular to said frame-piece;

a prolongation-piece is attached to said frame-piece of the U-shaped steel-bow and is extended so as to form the handle of the strip-holder;

said handle is made of the material of the steel-bow and, in the shape of a loop, is brought to the beginning of the frame-piece of the U-shaped steel-bow, where it forms a segment for the reinforcement of said prolongation-piece attached to said frame-piece of the U-shaped steel-bow; and, said turning and locking-peg is placed through boreholes made in two parallel-running rod-pieces forming said reinforcement-segment.

2. Strip-holder pursuant to claim 1, wherein a catch-pin is placed at the beginning of the handle in the prolongation-piece, and includes a catch-piece, under which a lever of the quick-tensing and gripping-device can lock.

3. Strip-holder pursuant to claim 2, wherein the lever of the quick-tensing and gripping-device, comprises T-shaped projection of the turning and locking-peg forming the interior bow-end.

4. Strip-holder pursuant to claim 2, wherein the two parallel-running rod-pieces are placed one upon another in the reinforcement segment and are fastened together by the turning-peg, at the beginning of the reinforcement segment, and by the catch-pin, at the end of the reinforcement-segment.

5. Strip-holder pursuant to claim 2, wherein the length of the steel-strip is greater than the distance between the external perimetral surfaces of the bow-ends of the U-shaped steel-bow, and the extent of a tension-range from the grip-slots around at least a portion of the perimeter of a bow-end is such that, by swinging the turning and locking-peg under the catch-piece of the catch-pin, torsion is applied to the bow-ends and the steel-strip is brought to a tense state.

6. Strip-holder pursuant to claim 2, wherein the turning and locking-peg is mounted flexibly in such a way that, in a tense state of the strip-holder, a lever projecting from the peg exerts pressure against the catch-piece.

7. Strip-holder pursuant to claim 1, wherein the turning and locking-peg has a tapered shaft-segment introduced through the boreholes of the reinforcement-segment, where it is fixed through mobile riveting on its external side, crossing through the two parallel-running rod-pieces.

8. Strip-holder pursuant to claim 1, wherein the rod-profile of the opposite ends of the U-shaped steel-bow and of the turning and locking-peg are round.

9. Strip-holder pursuant to claim 8, wherein the opposite ends of the steel-bow have the same diameter.

10. Strip-holder pursuant to claim 1, wherein said tape-like strip is an abrasive strip in the shape of a steel-band having a thickness of between 0.05 and 0.2 mm. for a grip-slot width of about 0.25 mm.

11. Strip-holder pursuant to claim 10, which is made of V2A-steel material.

12. A strip-holder pursuant to claim 1 in which the grip-slot in each of said steel-bow ends extends from one side of said steel-bow end to a small bore eccentric to the axis of the drawn-rod material of said steel-bow end.

* * * * *